United States Patent
Nicolaides et al.

(10) Patent No.: US 7,330,260 B2
(45) Date of Patent: Feb. 12, 2008

(54) METHOD FOR MEASURING ION-IMPLANTED SEMICONDUCTORS WITH IMPROVED REPEATABILITY

(75) Inventors: Lena Nicolaides, Castro Valley, CA (US); Mira Bakshi, Hayward, CA (US); Alex Salnik, Castro Valley, CA (US); Jon Opsal, Livermore, CA (US)

(73) Assignee: KLA-Tencor Corporation, San Jose, CA (US)

( * ) Notice: Subject to any disclaimer, the term of this patent is extended or adjusted under 35 U.S.C. 154(b) by 206 days.

(21) Appl. No.: 11/067,961

(22) Filed: Feb. 28, 2005

(65) Prior Publication Data
US 2005/0195399 A1 Sep. 8, 2005

Related U.S. Application Data

(60) Provisional application No. 60/549,397, filed on Mar. 2, 2004.

(51) Int. Cl.
*G01J 4/00* (2006.01)

(52) U.S. Cl. .................................. 356/369

(58) Field of Classification Search ............ 356/369; 250/559.09, 225
See application file for complete search history.

(56) References Cited

U.S. PATENT DOCUMENTS

| 5,978,074 A | 11/1999 | Opsal et al. ............ 356/72 |
| 6,878,559 B2* | 4/2005 | Borden et al. ............ 438/14 |
| 2004/0251927 A1 | 12/2004 | Salnik et al. ............ 324/765 |
| 2005/0122515 A1* | 6/2005 | Borden et al. ............ 356/369 |

* cited by examiner

Primary Examiner—Roy M Punnoose
(74) Attorney, Agent, or Firm—Stallman & Pollock LLP

(57) ABSTRACT

The repeatability of wafer uniformity measurements can be increased by taking spatially averaged measurements of wafer response. By increasing the time over which measurements are obtained, the amount of noise can be significantly reduced, thereby improving the repeatability of the measurements. These measurements can be taken at several locations on the wafer to ensure wafer uniformity. In order to get a stable and repeatable assessment of the wafer process, addressing uncertainties related to damage relaxation or incomplete anneal, an anneal decay factor (ADF) characterization can be performed at a distance away from the TW measurement boxes. From the ADF measurement and the spatially averaged measurements of wafer response, a repeatable assessment of the wafer process can be obtained.

38 Claims, 8 Drawing Sheets

- *Prior Art* -

- *Prior Art* -

METHOD FOR MEASURING ION-IMPLANTED SEMICONDUCTORS WITH IMPROVED REPEATABILITY

CLAIM OF PRIORITY

The present application claims priority to U.S. Provisional Application Ser. No. 60/549,397, filed Mar. 2, 2004, entitled "METHOD FOR MEASURING ION-IMPLANTED SEMICONDUCTORS WITH IMPROVED REPEATABILITY," which is hereby incorporated herein by reference.

TECHNICAL FIELD OF THE INVENTION

The present invention relates to characterization of an annealing process, such as the annealing of ion-implanted semiconductors.

BACKGROUND

Thermal wave and plasma wave monitoring systems typically are based on the detection of changes in intensity of a probe beam reflected off the surface of a semiconductor or other appropriate sample. Changes in the reflectivity of the surface are caused by thermal and plasma waves arising as a result of the absorption of an intensity-modulated pump beam directed at or near the same area on the surface as the probe beam. This technique is known in the prior art as the modulated optical reflectance (MOR) or thermal wave (TW) method. Exemplary thermal wave and plasma wave monitoring systems are described in U.S. Pat. Nos. 4,636,088, 4,854,710, and 5,978,074, each of which is hereby incorporated herein by reference. An exemplary optical arrangement of the prior art for capturing TW information is shown in FIG. 1, and described more fully in U.S. patent application Ser. No. 10/796,603, Publication No. 2004/0251927, which is hereby incorporated herein by reference. The system 100 includes a pump laser 102 and a probe laser 104, where the pump laser intensity is varied to create an intensity-modulated pump beam that is projected against the surface of a sample and absorbed, causing localized excitation of the sample. As the pump laser is modulated, the localized excitation (and subsequent relaxation) creates a train of thermal and plasma waves within the sample. These waves reflect and scatter off various features and interact with various regions within the sample in a way that alters the flow of heat and/or plasma from the pump beam spot. The presence of the thermal and plasma waves has a direct effect on the surface reflectivity of the sample. Features and regions below the sample surface that alter the passage of the thermal and plasma waves will therefore alter the optical reflective patterns at the surface of the sample. By monitoring the changes in reflectivity of the sample at the surface, information about characteristics below the surface can be obtained.

To monitor the surface changes, a probe laser is used to direct a probe beam at a portion of the sample that is excited by the pump laser. The sample reflects the probe beam and a photodetector 106 records the intensity of the reflected probe beam. The output signal from the photodetector is filtered to isolate the changes that are synchronous with the pump beam modulation. The detector generates separate "in-phase" (I) and "quadrature" (Q) outputs that can be supplied to a processor 108 and used to calculate amplitude and phase of the modulated signal. The amplitude and phase values are used to deduce physical characteristics of the sample. In most cases, this is done by measuring amplitude values (amplitude is used more commonly than phase) for one or more specially prepared calibration samples, each of which has known physical characteristics. The empirically derived values are used to associate known physical characteristics with corresponding amplitude values. Amplitude values obtained for test samples can then be analyzed by comparison to the amplitude values obtained for the calibration samples.

As part of the manufacturing process, ions (or dopants) are added to the near-surface region of semiconductors using a process known as implantation. The implanted region (with its relatively high dopant concentration) overlays a non-implanted region where dopant concentrations are relatively low. Incompleteness of anneal, a parameter that is crucial to USJ characterization, appears when non-uniformities in structural damage caused by ion implantation along with malfunctioning of the rapid thermal anneal process and other types of annealing processes result in residual structural damage areas on the surface of a semiconductor wafer after anneal. This incomplete anneal should also be monitored to increase manufacturing yield and to ensure high performance characteristics of a semiconductor device.

Damage relaxation after ion implantation, as well as incomplete anneal due to residual damage and/or surface states, results in a gradual change in the measured TW signal on a semiconductor element, such as a silicon wafer, as a function of time. If measurements are made on a wafer immediately after implantation or anneal, and at periodic intervals thereafter, the TW signal will slowly change until a steady-state asymptotic value is reached. The amount of change in the TW signal, as well as the characteristic time for the signal to stabilize, will depend on factors such as the properties of the semiconductor wafer, as well as the implantation and anneal conditions.

One prior art technique eliminates the dependence of the TW signal on time. This technique is described, for example, in U.S. Provisional Application Ser. No. 60/495,053, filed Aug. 14, 2003, entitled "METHOD FOR COMPENSATING FOR INCOMPLETE ANNEAL IN ION-IMPLANTED SEMICONDUCTORS," which is hereby incorporated herein by reference. This technique allows for a characterization of anneal process, including measurements of completeness and uniformity, as well a compensation for incomplete anneal and damage relaxation. This technique utilizes a pump laser to accelerate the annealing process. When the pump beam illuminates a single spot, such as a 1 μm spot, on a semiconductor wafer subject to damage relaxation or having residual damage, the thermally-induced crystal restructuring effect can be accelerated so that a steady-state "annealed" signal can be obtained in a matter of seconds, rather than the hours or even days necessary to obtain a steady state signal at room temperature (i.e., an "environmental" anneal). Such an annealed TW signal is independent of the time elapsed since the implant and/or anneal processes were performed.

FIG. 2 shows an exemplary TW signal as monitored and recorded over time. The resultant curve 200 can be fit to an exponential decay, and an anneal decay factor (ADF) can be calculated. The ADF parameter characterizes the degree of damage relaxation or completeness of the anneal, and can be used to compensate for these phenomena. The anneal decay factor in this example is calculated from the following relation:

$$ADF = TW_{10}/TW_0$$

where $TW_0$ corresponds to the value of the TW signal at the beginning of the compensation process, and $TW_{10}$ corresponds to the value of the TW signal recorded and after 10 seconds of the compensation process. While 10 seconds can be appropriate in this example, other periods of time can be used that can be appropriate for different conditions, such as different implant conditions. Further, the decay can be measured for a period of about 10 seconds then extrapolated to a period of about 30 seconds, for example. A separate ADF value can be calculated for each individual set of implantation and anneal conditions to characterize the completeness of the anneal process.

When characterizing the anneal process, it typically cannot be assumed that the annealing process is uniform across an entire surface. Non-uniformities can be more common when using a rapid thermal anneal (RTA) process. In this case, the ADF technique can monitor a degree of anneal non-uniformity across the wafer by measuring point-by-point $TW_0$ and $TW_{10}$ contour maps. FIG. 3 shows (a) $TW_0$ and (b) $TW_{10}$ maps 300, 310 obtained from the same region on a semiconductor wafer after anneal, where regions of substantial residual damage (e.g., incomplete anneal, RTA failure) can be seen. From these maps, an ADF contour map 400 can be calculated, as shown in FIG. 4. The ADF contour map can be used to characterize the quality of anneal process. Such a map implies that the closer the ADF is to unity, the better the annealing quality.

Such a technique can be used to monitor and/or control uniformity and completeness of anneal after each technological step in a fabrication process. In this case the ADF measurement results obtained after each process step, whether at individual sites or entire wafer maps, can be analyzed and compared, thus facilitating process system troubleshooting in applications such as semiconductor manufacturing.

One of the most important characteristics of the TW system performance in pre- or post-anneal applications is the repeatability of the measurements. Wafer non-uniformities, as well as TW system drift and other variables, can result in changes in the TW signal over time. Single-point measurements at several locations across the wafer surface cannot produce a desirable repeatability over time, even when supported by an ADF characterization.

DETAILED DESCRIPTION

Systems and methods in accordance with embodiments of the present invention overcome deficiencies in prior art TW techniques to achieve high TW system repeatability in both pre- and -post anneal measurements. This repeatability is independent of damage relaxation and/or incomplete anneal of the sample being analyzed. Such systems also can obtain high TW system throughput by reducing the amount of time needed to measure each sample, such as each semiconductor wafer.

An approach in accordance with one embodiment of the present invention utilizes a spatial averaging measurement algorithm, which can be combined with an ADF characterization taken at a separate location on the sample. Herein, the approach will be discussed with respect to a semiconductor wafer as an example, which should not be taken as a limitation on the scope of the present invention.

Figure 1:
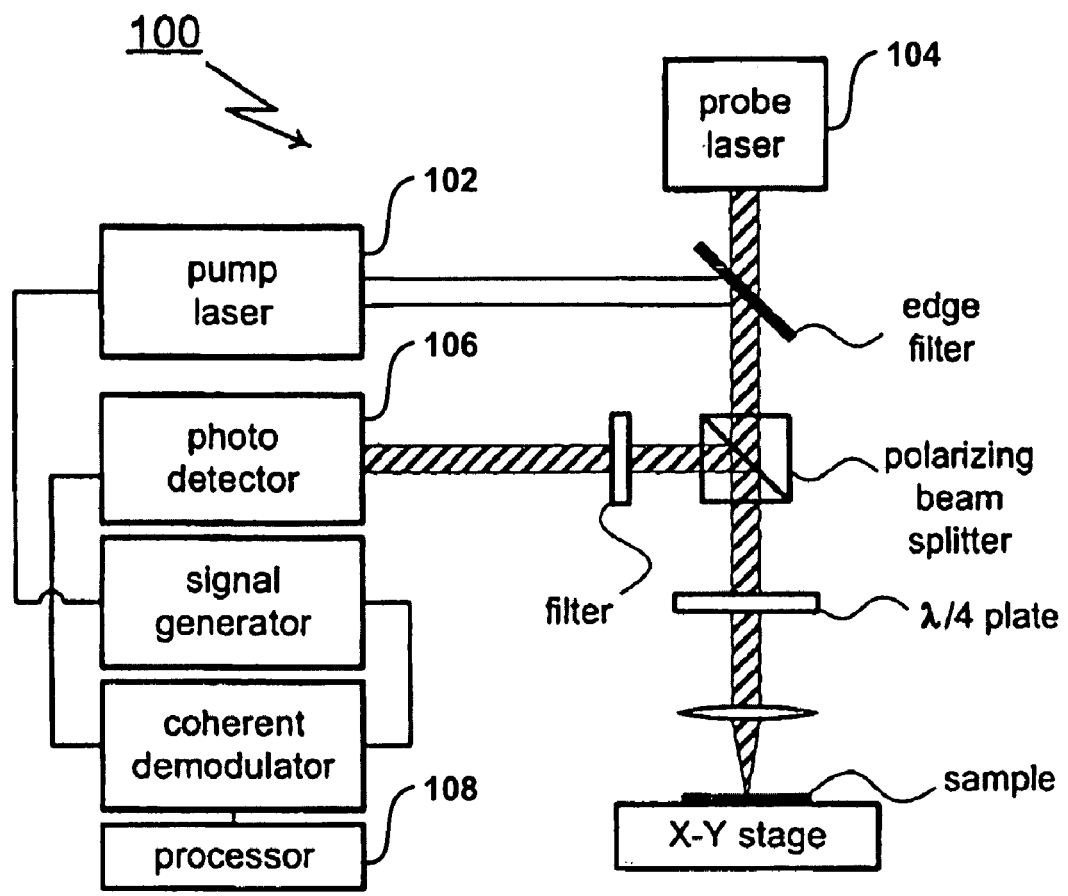
FIG. 1 is a diagram of a system for capturing thermal wave information of the prior art.
Figure 2:
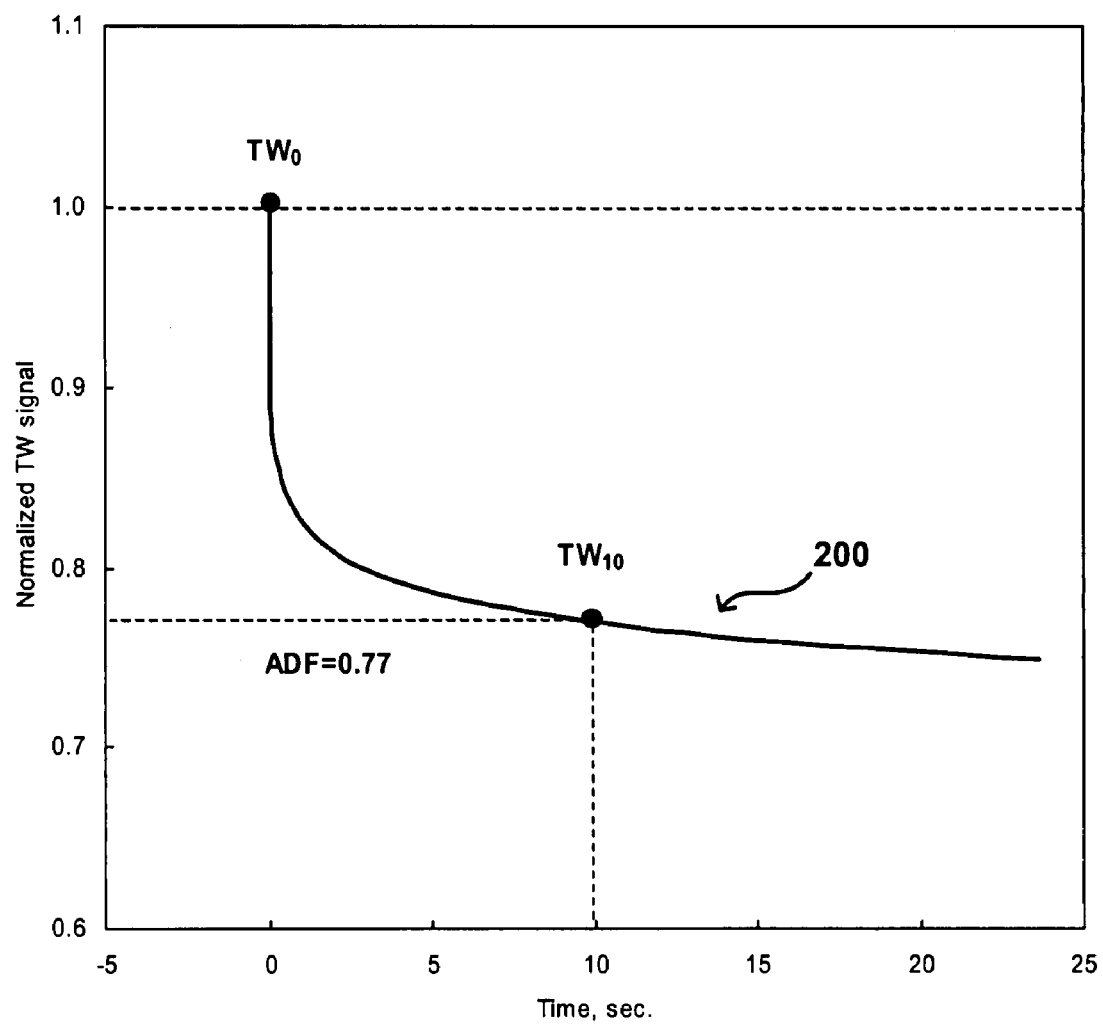
FIG. 2 is a graph of the prior art showing the behavior of a thermal wave signal over time.
Figure 3:
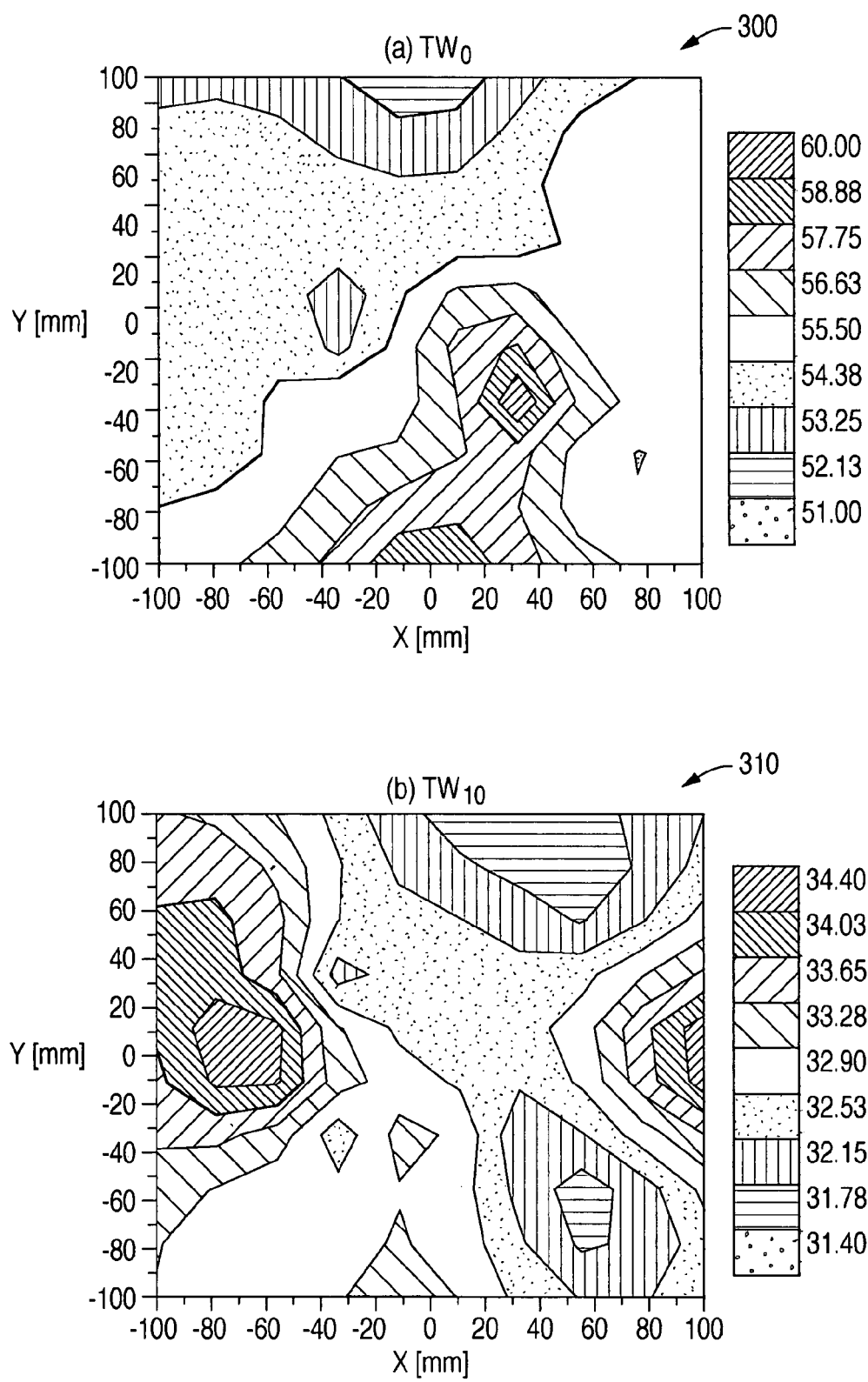
FIG. 3 contains thermal wave contour maps of the prior art.
Figure 4:
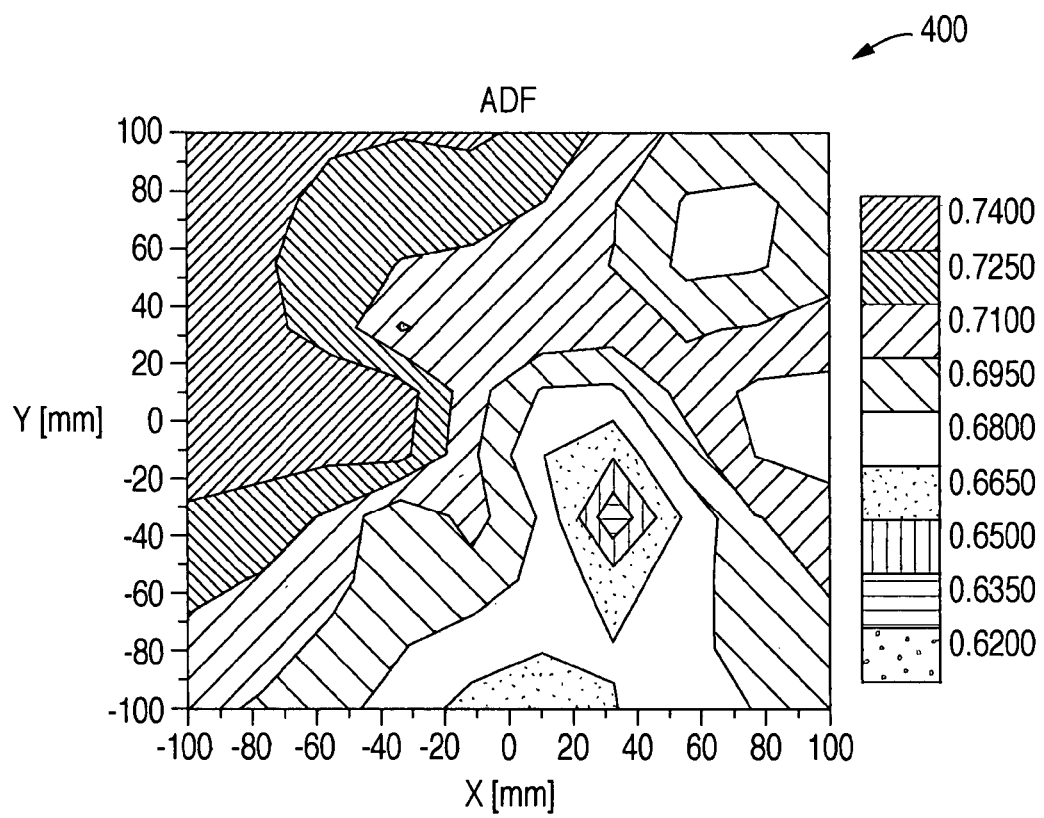
FIG. 4 is a contour map of the prior art showing the anneal decay factor (ADF) contour for the region of FIG. 3.
Figure 5:
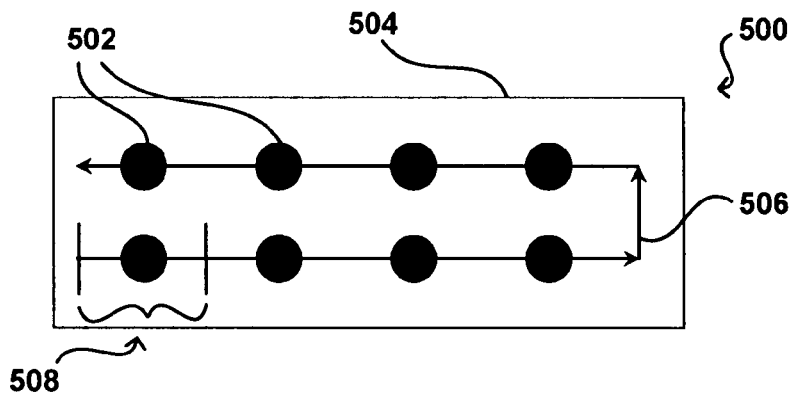
FIG. 5 is a diagram showing a measurement sequence that can be used in accordance with one embodiment of the present invention.

An exemplary spatial averaging technique utilizes a sequence of measurements following a pattern 500 such as that shown in FIG. 5, instead of a series of measurements taken at a single spot location. As seen in the Figure, a number of TW measurements are performed at a number of measurement spots 502 within a small box 504 on a wafer surface. This box can be any area on an unpatterned or process wafer, but in at least one embodiment is preferred to be located in an implant area for a patterned or product wafer. Measurements can be taken sequentially by moving along a measurement path 506 inside the box 504. These measurements can be taken by making a TW measurement at each measurement spot, then moving to the next spot and taking another TW measurement. In a dynamic approach, overlapping pump and probe beam spots can move along the path 506 in the box, with TW measurements being taken continually. The system then can calculate an average TW measurement at each spot using the data for a given region. For example, the first spot measurement along the path 506 in FIG. 5 can represent the average TW measurement during the portion of the path represented by region 508. Parameters such as the size of the box and the shape of the path can vary, depending on factors such as the number of desired measurements, the size of each measurement spot, and the amount of time over which measurements are to be taken. These factors, as well as the shape of the path, the number of spatial averaging locations, and the location of the measurement can be user configurable. In a semiconductor example, a box can be selected to fit within a measurement pad on a product wafer, as known in the art, which can have dimensions on the order of about 50 $\mu$m×50 $\mu$m, and can be set to take measurements over a selectable period of time, such as 12 or 24 seconds, with TW measurements being averaged or determined every 2-4 seconds, which also can be user selectable. The resultant path then can be configured automatically or by the user. Increasing the time over which the measurements are taken and averaged reduces noise, thereby increasing repeatability.

Figure 6:
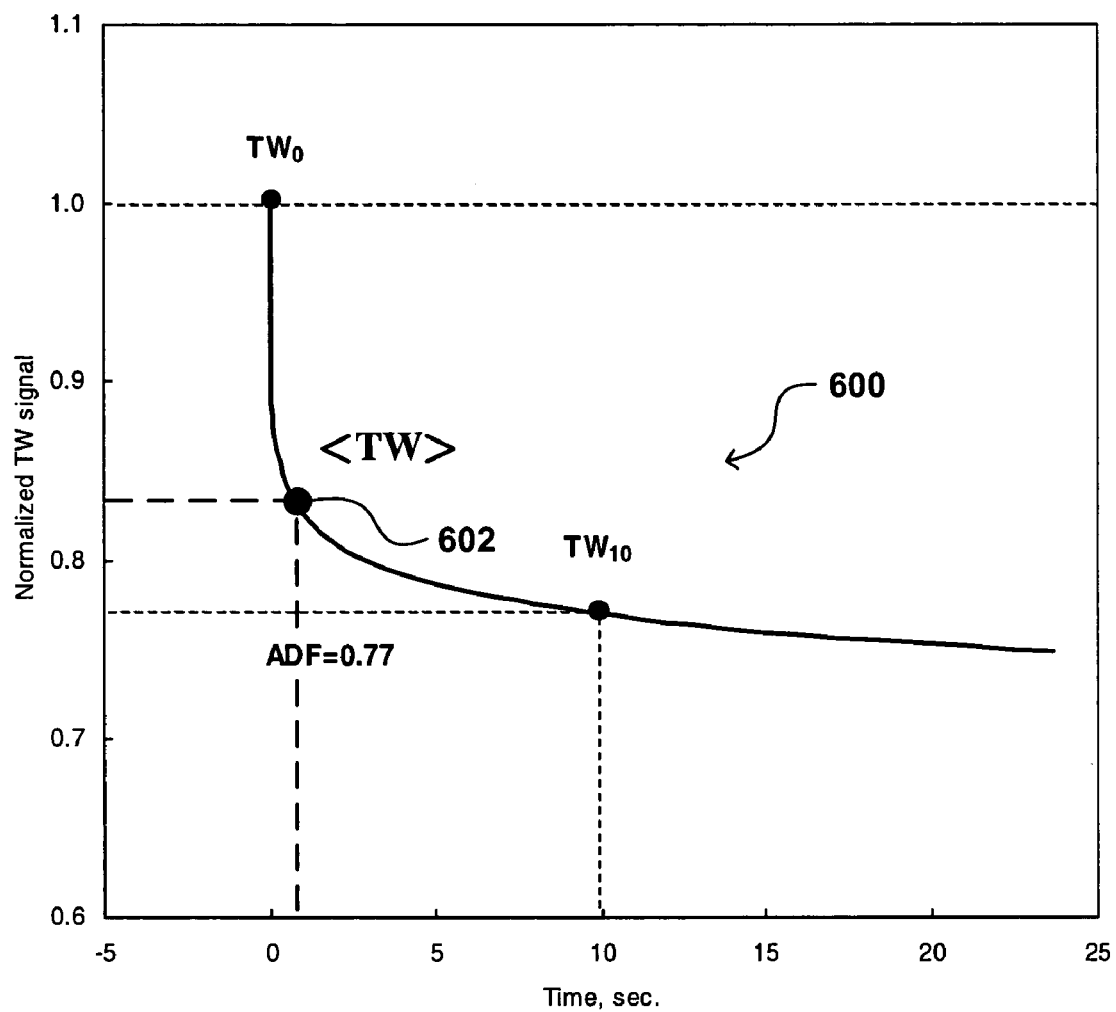
FIG. 6 is a plot showing the behavior of a thermal wave signal and the average thermal wave measurement using the measurement sequence of FIG. 5.

The TW measurements made within the box can be performed somewhat rapidly, the entire path typically being completed in a matter of seconds. An average value <TW> of the TW measurements then can be calculated from the TW signals obtained for each measurement spot in the box. Since there is only a relatively short dwell time at each measurement point, the TW signal obtained at each point, as well as the average value <TW>, will not reach an actual steady-state level until much later. As can be seen in the plot 600 of FIG. 6, the time to achieve a steady-state level (greater than 25 seconds in this example) is much longer than the period per point for measurements (2-3 seconds in this example). As can be seen in FIG. 6, an average TW value <TW> 602 can be calculated that, when compared to the normalized TW signal curve 600, also gives the amount of time necessary for the surface region to achieve that average state.

Figure 7:
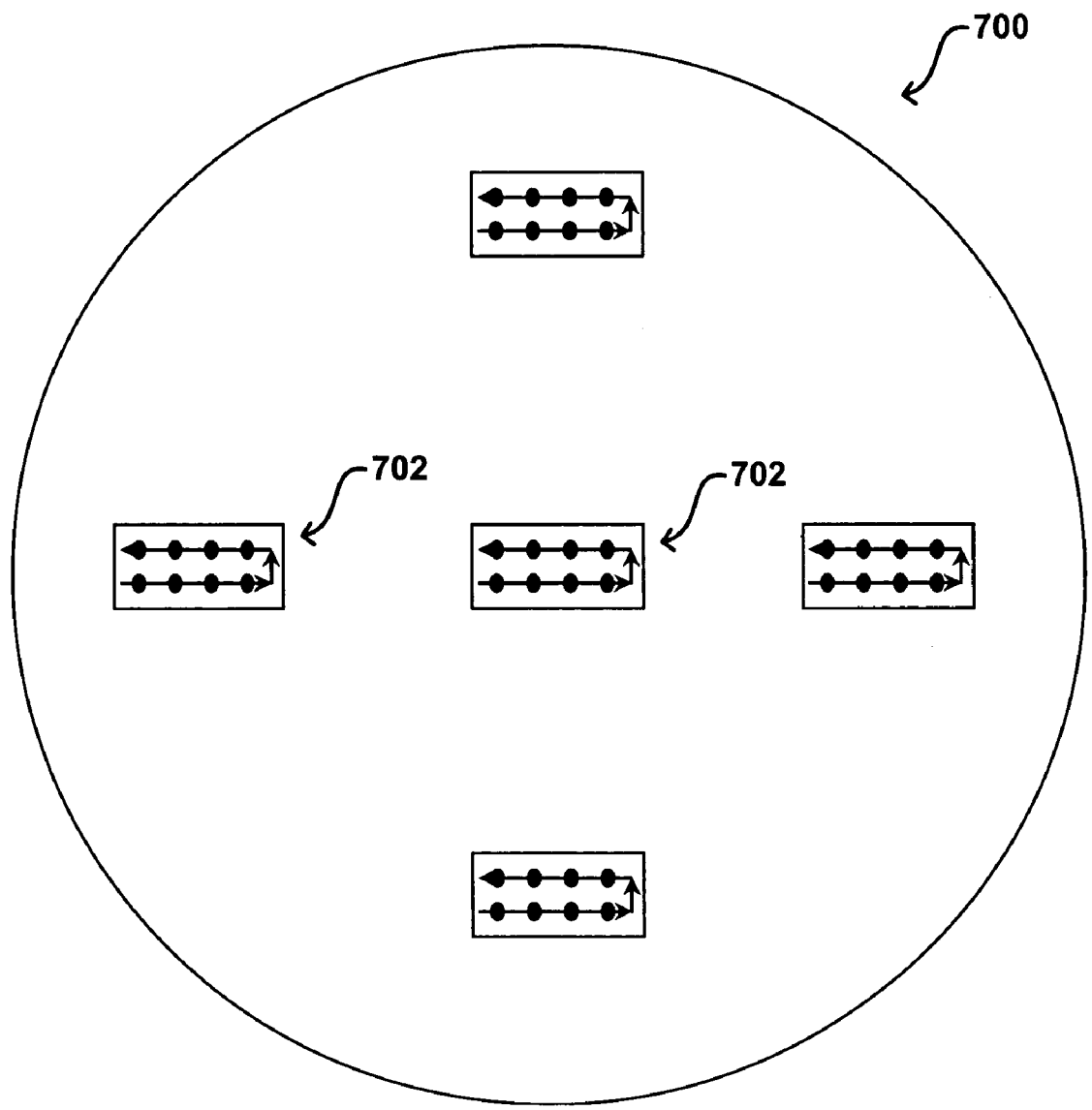
FIG. 7 is a diagram showing the locations of several measurement sequences repeated across the surface of a wafer in accordance with one embodiment of the present invention.

The spatially averaged measurements of <TW> can be repeated at several locations 702 on the surface of the wafer 700, such as depicted in the example of FIG. 7. The number and position of these locations can be user configurable. As a result, a map or array of <TW> values across the wafer surface can be generated, which gives a measure of the uniformity of the wafer. The greater the number of spatial averaging measurements, the better the uniformity of the wafer can be determined. The number of <TW> measurements taken, then, can be dependent upon factors such as the quality of the wafer fabrication process and the desire of the end user or customer. The spatial averaging is a true measurement of the wafer response that many customers want to see, for a number of wafer response sites, to ensure the wafer meets minimum uniformity criteria.

While the resultant array or map of spatially averaged TW measurements can provide a measure of wafer uniformity, giving an indication of ion implant or anneal process quality, such a map does not represent a stable and repeatable assessment of the wafer process, as the map still contains uncertainties related to possible damage relaxation or incomplete anneal.

Figure 8:
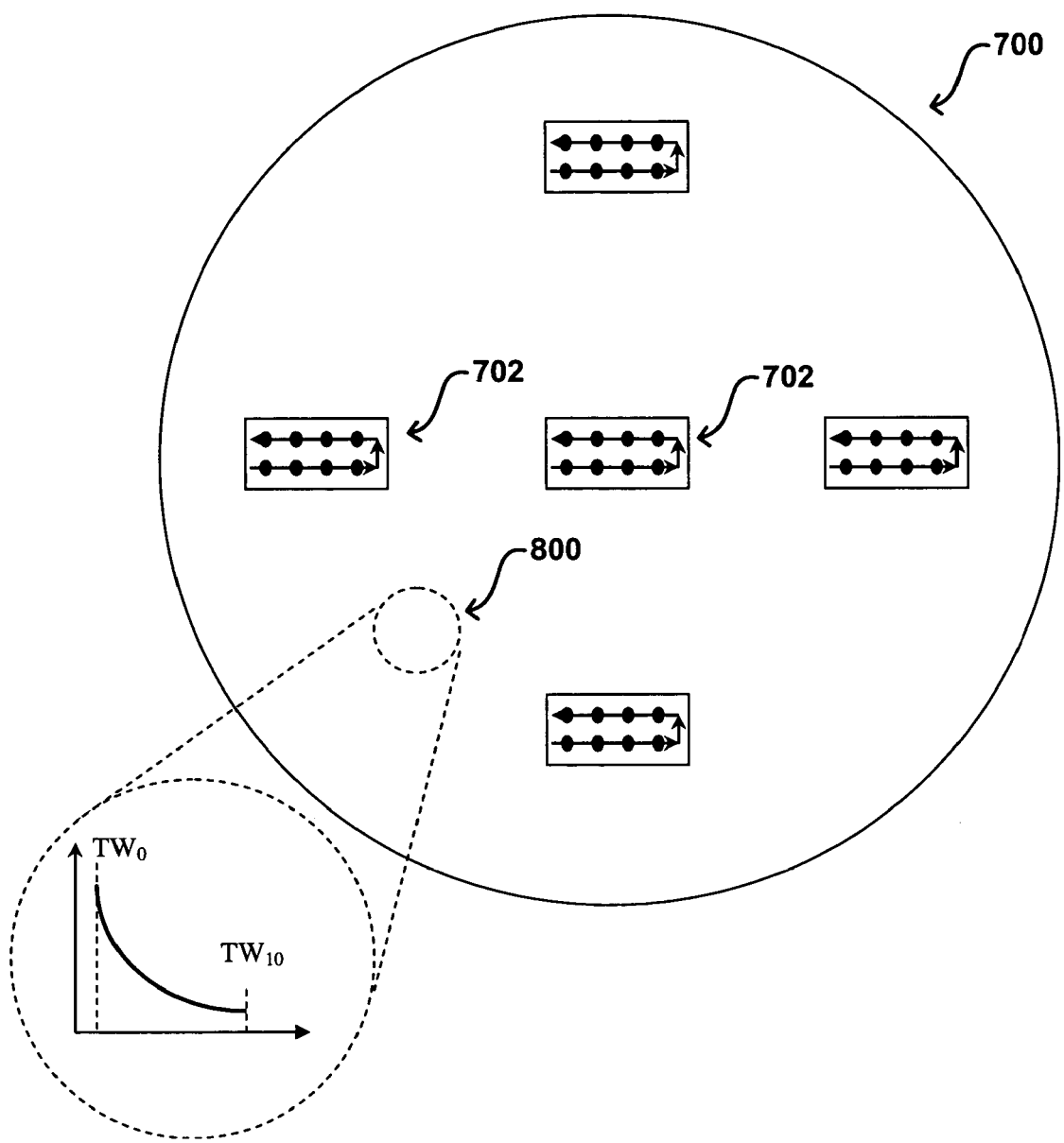
FIG. 8 is a diagram showing the location of an ADF characterization relative to the measurement locations of FIG. 7.

Systems and methods in accordance with various embodiments of the present invention can remove these uncertainties by utilizing at least one ADF characterization taken at a different location. As shown in FIG. 8, an ADF characterization can be performed in a selected location 800 on the surface of the wafer 700 of FIG. 7. The ADF characterization can be performed at a distance away from the TW measurement boxes 702. For a monitor wafer, this measurement can be made at any location not already exposed during the <TW> measurement process, in order to give a true representation of damage relaxation time. For a product wafer, it can be desirable to take the ADF measurement on an implant region, or a region similar to the spatial averaging measurement locations. Again, the ADF measurement location can be user selectable. The ADF value can be calculated from TW signals recorded at the beginning of the compensation process and after 10 seconds, $TW_0$ and $TW_{10}$ respectively, as described above. The $TW_0$ value used in the ADF calculation can be synchronized with the same dwell time spent on each spatial averaging measurement spot.

One or more measurements of ADF can be performed at a selected location, such as within the selected location circle 800 shown in FIG. 8. Additional ADF measurement locations can be selected, with at least one ADF measurement taken at each location. All ADF measurements then can be averaged to give an overall ADF measurement.

Once a value of ADF is obtained for the wafer, the truly relaxed or incomplete anneal compensated signal $TW_{inf}$ can be calculated for each measurement location 702 on the surface of the wafer 700. The compensated signal can be calculated using the formula:

$$TW_{inf}=ADF*<TW>$$

Figure 9:
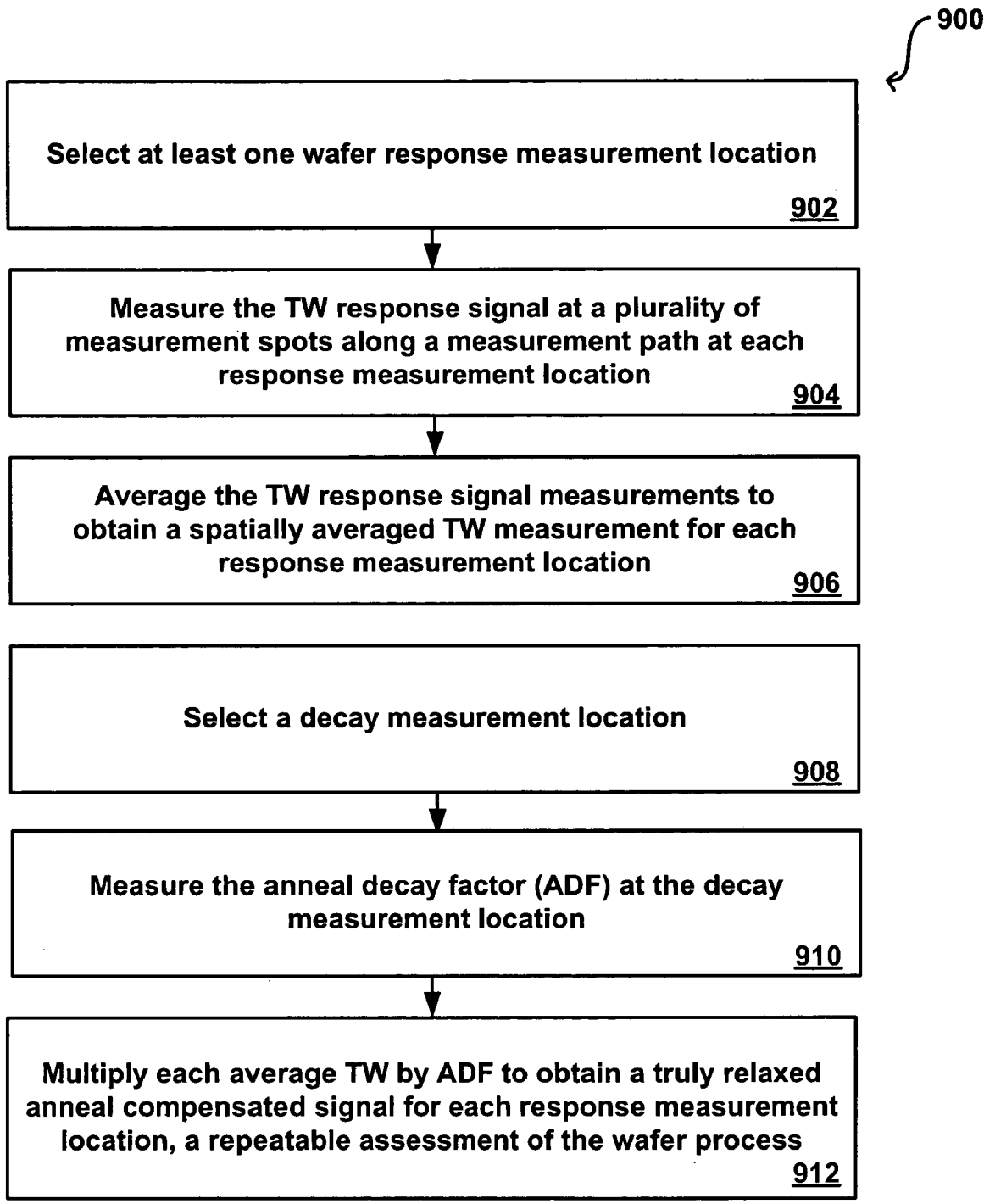
FIG. 9 is a flowchart showing the steps of a characterization process in accordance with one embodiment of the present invention.

FIG. 9 shows steps of an exemplary overall process 900 in accordance with one embodiment of the present invention. In this process 900, a user (or customer) selects at least one location at which to capture TW data relating to the response of the wafer 902. As discussed above, this can be at any location for a sample such as a process wafer or on an implant region for a product wafer. For each of the selected locations, the TW response signal can be measured at a plurality of measurement spots along a measurement path 904. The measurement path can be selected by the user or determined by the system based on factors discussed above. The TW response signal measurements for each measurement spot in a selected location can be averaged to obtain a spatially-averaged TW measurement <TW> 906 for that location. A location on the wafer also can be selected in which to take at least one decay measurement 908. This location can be at any location similar to the locations selected for the TW measurements, but should be at a site that was not significantly exposed during the TW measurements. In an alternative embodiment, the decay can be measured at one of the TW measurement sites, such as at the last measurement spot. The anneal decay factor (ADF) for the wafer can be measured at the selected ADF location 910. Once obtained, the ADF value can be multiplied by the average TW value at each location to obtain a truly relaxed anneal compensated signal for each selected TW measurement location on the wafer 912. The result is an array of stable and repeatable measurements of wafer uniformity.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

What is claimed is:

1. A method for evaluating characteristics of a sample, comprising:
    directing an intensity modulated pump beam and a probe beam along a measurement path at a response measurement location on the sample and detecting a reflected portion of the probe beam and monitoring changes in the modulated intensity of the reflected probe beam resulting from the changes in the optical reflectivity of the sample induced by the pump beam;
    calculating an intensity value for the monitored changes of the reflected portion at a plurality of measurement spots along the measurement path, said intensity value corresponding to the modulated optical reflectivity of the sample, and wherein the characteristics of the sample along the measurement path are substantially uniform;
    averaging the intensity values to obtain a spatially averaged intensity value for the response measurement location; and
    storing the spatially averaged intensity value for subsequent use.

2. A method according to claim 1, wherein:
    calculating an intensity value includes dividing the measurement path into a plurality of measurement regions, each measurement region including one of the measurement spots, and calculating a regional average intensity value measured over the measurement region including the measurement spot.

3. A method according to claim 1, further comprising:
    selecting the response measurement location.

4. A method according to claim 1, wherein:
the pump beam causes changes in the optical reflectivity of the sample.

5. A method according to claim 1, wherein:
the pump beam forms a pump beam spot on the sample that at least partially overlaps a probe beam spot formed by the probe beam.

6. A method according to claim 1, wherein:
the pump beam is operable to accelerate an annealing process of the sample at the response measurement location.

7. A method according to claim 1, wherein:
the response measurement location is in an implant region of the sample.

8. A method according to claim 1, wherein:
the sample is one of a process wafer and a product wafer.

9. A method according to claim 1, further comprising:
directing the pump beam and the probe beam to a decay measurement location separate from the response measurement location and detecting a reflected portion of the probe beam;
calculating periodic intensity values for the reflected portion at a plurality of measurement times over a decay period; and
calculating an anneal decay factor from the periodic intensity values.

10. A method according to claim 9, wherein:
the decay period is on the order of about 10 seconds.

11. A method according to claim 9, further comprising:
multiplying the anneal decay factor by the spatially averaged intensity value to obtain an incomplete anneal compensated, spatially averaged intensity value for the response measurement location.

12. A method for evaluating characteristics of a sample, comprising:
directing an intensity modulated pump beam and a probe beam to a first measurement spot in a response measurement location on the sample and detecting a reflected portion of the probe beam and monitoring changes in the modulated intensity of the reflected probe beam resulting from the changes in the optical reflectivity of the sample induced by the pump beam;
calculating a first intensity value for the monitored changes of the first reflected portion at the first measurement spot said intensity value corresponding to the modulated optical reflectivity of the sample;
directing the pump beam and the probe beam along a measurement path to at least one additional measurement spot in the response measurement location, and detecting and monitoring a subsequent reflected portion of the probe beam at each additional measurement spot, and wherein the characteristics of the sample along the measurement path are substantially uniform;
calculating a subsequent intensity value for each subsequent reflected portion at each additional measurement spot;
averaging the first and subsequent intensity values to obtain a spatially averaged intensity value for the response measurement location; and
storing the spatially averaged intensity value for subsequent use.

13. A method according to claim 12, wherein:
the pump beam forms a pump beam spot on the sample that at least partially overlaps a probe beam spot formed by the probe beam.

14. A method according to claim 12, wherein:
the pump beam is operable to accelerate an annealing process of the sample at the response measurement location.

15. A method according to claim 12, wherein:
the response measurement location is in an implant region of the sample.

16. A method according to claim 12, further comprising:
directing the pump beam and the probe beam to a decay measurement location separate from the response measurement location and detecting a reflected portion of the probe beam;
calculating periodic intensity values for the reflected portion at a plurality of measurement times over a decay period; and
calculating an anneal decay factor from the periodic intensity values.

17. A method according to claim 16, wherein:
the decay period is on the order of about 10 seconds.

18. A method according to claim 16, further comprising:
multiplying the anneal decay factor by the spatially averaged intensity value to obtain an incomplete anneal compensated, spatially averaged intensity value for the response measurement location.

19. A method for evaluating characteristics of a sample, comprising:
directing an intensity modulated pump beam and a probe beam along a measurement path at each of a plurality of response measurement locations on the sample and detecting a reflected portion of the probe beam and monitoring changes in the modulated intensity of the reflected probe beam resulting from the changes in the optical reflectivity of the sample induced by the pump beam;
calculating an intensity value for the monitored changes of the reflected portion at a plurality of measurement spots the measurement path for each response measurement location said intensity value corresponding to the modulated optical reflectivity of the sample and wherein the characteristics of the sample alone the measurement path are substantially uniform;
averaging the intensity values to obtain a spatially averaged intensity value for each response measurement location; and
storing the spatially averaged intensity value for subsequent use.

20. A method according to claim 19, further comprising:
generating an array of spatially averaged intensity values for the sample.

21. A method according to claim 19, wherein:
calculating an intensity value for each response measurement location includes dividing the measurement path into a plurality of measurement regions, each measurement region including one of the measurement spots, and calculating a regional average intensity value measured over the measurement region including the measurement spot.

22. A method according to claim 19, wherein:
the pump beam forms a pump beam spot on the sample that at least partially overlaps a probe beam spot formed by the probe beam.

23. A method according to claim 19, wherein:
the pump beam is operable accelerate an annealing process of the sample at the response measurement location.

24. A method according to claim 19, further comprising:
directing the pump beam and the probe beam to a decay measurement location separate from the response measurement location and detecting a reflected portion of the probe beam;
calculating periodic intensity values for the reflected portion at a plurality of measurement times over a decay period; and
calculating an anneal decay factor from the periodic intensity values.

25. A method according to claim 24, wherein:
the decay period is on the order of about 10 seconds.

26. A method according to claim 24, further comprising:
multiplying the anneal decay factor by each spatially averaged intensity value to obtain an incomplete anneal compensated, spatially averaged intensity value for each response measurement location.

27. A method for evaluating characteristics of a sample, comprising:
directing a probe beam and an intensity modulated pump beam along a measurement path at each of a plurality of response measurement locations on the sample and detecting a reflected portion of the probe beam and monitoring changes in the modulated intensity of the reflected probe beam resulting from the changes in the optical reflectivity of the sample induced by the pump beam, the pump beam operable to accelerate an annealing process of the sample at each measurement location, thereby changing the optical reflectivity of the sample;
calculating an intensity value for the monitored changes of the reflected portion at a plurality of measurement spots along the measurement path for each response measurement location said intensity value corresponding to the modulated optical reflectivity of the sample and wherein the characteristics of the sample alone the measurement path are substantially uniform;
averaging the intensity values to obtain a spatially averaged intensity value for each response measurement location;
directing the probe beam and the pump beam to a decay measurement location, separate from each response measurement location, and monitoring the intensity of the reflected probe beam over time to determine an anneal decay factor for the sample;
multiplying the anneal decay factor by each spatially averaged intensity value to obtain an incomplete anneal compensated, spatially averaged intensity value for each response measurement location; and
storing the incomplete anneal compensated spatially averaged intensity values for subsequent use.

28. A method according to claim 27, further comprising:
determining at least one additional anneal decay factor for the sample and determining an average anneal decay factor for the sample to be multiplied by each spatially averaged intensity value.

29. A method according to claim 27, wherein:
calculating an intensity value for each response measurement location includes dividing the measurement path into a plurality of measurement regions, each measurement region including one of the measurement spots, and calculating a regional average intensity value measured over the measurement region including the measurement spot.

30. A method according to claim 27, wherein:
the pump beam forms a pump beam spot on the sample that at least partially overlaps a probe beam spot formed by the probe beam.

31. A system for evaluating characteristics of a sample, comprising:
a probe source operable to direct a probe beam along a measurement path for a plurality of response measurement locations on the sample;
an intensity modulated pump beam source operable to direct a pump beam to each response measurement location and move the pump beam along each measurement path with the probe beam, the pump beam causing changes in the optical reflectivity of the sample and wherein the characteristics of the sample along the measurement path are substantially uniform;
a detector device operable to detect a reflected portion of the probe beam, reflected from the sample, and generate a modulated output signal in response thereto resulting from the changes in the optical reflectivity of the sample induced by the pump beam; and
a processor in communication with the detector device and operable to receive the output signal and calculate an intensity value from the modulated output signals at a plurality of response measurement locations along each measurement path, said intensity value corresponding to the modulated optical reflectivity of the sample the processor further operable to average the intensity values to obtain a spatially averaged intensity value for each response measurement location.

32. A system according to claim 31, wherein:
the processor calculates an intensity value by dividing the measurement path into a plurality of measurement regions, each measurement region including one of the measurement spots, and calculating a regional average intensity value measured over the measurement region including the measurement spot.

33. A system according to claim 31, wherein:
the pump beam forms a pump beam spot on the sample that at least partially overlaps a probe beam spot formed by the probe beam.

34. A system according to claim 31, wherein:
the pump beam is operable to pump laser to accelerate an annealing process of the sample at each response measurement location.

35. A system according to claim 31, wherein:
the pump source and probe source are further operable to direct the pump and probe beams, respectively, to a decay measurement location separate from each response measurement location.

36. A system according to claim 35, wherein:
the detector device is further operable to detect a reflected portion of the probe beam, reflected from the decay measurement location, and generate an output signal in response thereto.

37. A system according to claim 36, wherein:
the processor is further operable to monitor the intensity of the reflected portion over time and calculate an anneal decay factor for the decay measurement location.

38. A system according to claim 37, wherein:
the processor is further operable to multiply the anneal decay factor by the spatially averaged intensity value to obtain an incomplete anneal compensated, spatially averaged intensity value for the response measurement location.

* * * * *